(12) United States Patent
Stauffer et al.

(10) Patent No.: US 10,994,070 B2
(45) Date of Patent: May 4, 2021

(54) DEVICE AND METHOD FOR TESTING AND INSPECTING THE INTEGRITY OF AN AUTOINJECTOR

(71) Applicant: Packaging Technologies & Inspection, LLC, Hawthorne, NY (US)

(72) Inventors: Oliver Stauffer, Tuckahoe, NY (US); Anton Stauffer, Morges (CH)

(73) Assignee: Packaging Technologies & Inspection, LLC, Hawthorne, NY (US)

( * ) Notice: Subject to any disclaimer, the term of this patent is extended or adjusted under 35 U.S.C. 154(b) by 0 days.

(21) Appl. No.: 16/966,728

(22) PCT Filed: Feb. 6, 2019

(86) PCT No.: PCT/US2019/016820
§ 371 (c)(1),
(2) Date: Jul. 31, 2020

(87) PCT Pub. No.: WO2019/157036
PCT Pub. Date: Aug. 15, 2019

(65) Prior Publication Data
US 2020/0360596 A1 Nov. 19, 2020

Related U.S. Application Data

(60) Provisional application No. 62/626,831, filed on Feb. 6, 2018.

(51) Int. Cl.
*A61M 5/00* (2006.01)
*G16H 20/17* (2018.01)
(Continued)

(52) U.S. Cl.
CPC ............... *A61M 5/002* (2013.01); *A61J 1/00* (2013.01); *A61M 5/20* (2013.01); *G16H 20/17* (2018.01)

(58) Field of Classification Search
CPC ........ A61M 5/002; A61M 5/20; G16H 20/17; A61J 1/00
See application file for complete search history.

(56) References Cited

U.S. PATENT DOCUMENTS 5,628,309 A    5/1997  Brown
6,288,554 B1   9/2001  Yasumoto
(Continued)

FOREIGN PATENT DOCUMENTS

WO    2006021295 A1    3/2006
WO    2014066256 A1    5/2014
WO    2017136007 A1    8/2017

OTHER PUBLICATIONS

International Search Report and Written Opinion in International Patent Application No. PCT/US2019/016820, dated Apr. 24, 2019 (12 pages).

*Primary Examiner* — Lauren P Farrar
(74) *Attorney, Agent, or Firm* — Benesch, Friedlander, Coplan & Aronoff LLP

(57) ABSTRACT

A device and method for testing and inspecting the integrity of an autoinjector device is disclosed. The autoinjector devices includes a medication container, a housing that receives the medication container, the housing including a plurality of electrodes arranged circumferentially relative to the medication container, and a plurality of electrical contacts corresponding to the plurality of electrodes and in electrical communication therewith, the electrical contacts being accessible from the exterior of the autoinjector device, wherein a circuit between at least one pair of electrodes, measured at the electrical contacts, indicates a defect in the medication container. A method of testing the integrity of the autoinjector device is also disclose, wherein a voltage is applied to the electrical contacts in order to determine the integrity of the medication container in the autoinjector (Continued)

device. Accordingly, defects in the pre-packaged medication container in the autoinjector device may be detected.

19 Claims, 6 Drawing Sheets

(51) Int. Cl.
*A61J 1/00* (2006.01)
*A61M 5/20* (2006.01)

(56) References Cited

U.S. PATENT DOCUMENTS

| | | | |
|---|---|---|---|
| 6,352,523 B1* | 3/2002 | Brown | A61M 5/1782 |
| | | | 222/23 |
| 2012/0209111 A1* | 8/2012 | Cowan | A61M 5/2425 |
| | | | 600/432 |

* cited by examiner

DEVICE AND METHOD FOR TESTING AND INSPECTING THE INTEGRITY OF AN AUTOINJECTOR

CROSS REFERENCE TO RELATED APPLICATIONS

This application is a national stage entry of International Patent Application No. PCT/US19/16820, filed on Feb. 6, 2019, which claims priority to U.S. Provisional Application No. 62/626,831, filed on Feb. 6, 2018, the contents of which are herein incorporated by reference.

BACKGROUND OF THE INVENTION

Field of the Invention

The present invention relates generally to container closure integrity testing, and more particularly to a device and method of testing and inspecting the integrity of an autoinjector for dispensing and injecting a medication.

Description of Related Art

High voltage leak detection (HVLD) is a means to detect leaks in packaging through the application of high voltage. An exemplary HVLD detection system and method are disclosed in international application no. PCT/US2016/056976, published as WO 2017136007 A1 on Aug. 10, 2017, and incorporated herein by reference. The HVLD detection method operates on the principles of electrical resistance and capacitance. To test a package using HVLD, the package must be made of non-conductive materials and the product inside must be conductive. A package will be exposed to high voltage between at least two probes, where one probe applies high voltage to the package and a second probe is a grounding source. If the package has a leak, the electrical resistance of the package walls is reduced, and voltage will conduct through the package.

HVLD inspection typically requires that the sterile barrier of the package be accessible by the HVLD probes for a proper inspection of the sterile barrier. In the case of injectable products, inspection is critical to patient safety. A common presentation for injections is a prefilled syringe loaded into an autoinjector assembly, together commonly referred to as an autoinjector. The autoinjector is a medical device designed to allow self-administration of a drug dose. The autoinjector assembly typically includes a plastic housing that protects the needle and liquid container, however internally organized or configured. Exemplary autoinjector assemblies are disclosed in U.S. Pat. Nos. 7,449,012 and 8,945,067. While the plastic housing may have a window feature to visibly see the syringe and liquid product, it does not provide access for container closure integrity (CCI) testing of the autoinjector. The lack of access to the syringe or similar liquid medication container in the autoinjector assembly to perform CCI testing, such as by HVLD methods, currently poses serious technical difficulties in testing these products for leaks or other package deficiencies. Under current configurations, an HVLD inspection of autoinjector assemblies would require disassembly of the autoinjector or similar inefficient means of inspection for a high-risk application. The present invention described herein seeks to solve these difficulties.

BRIEF SUMMARY OF THE INVENTION

It is an object of the claimed invention to provide CCI testing of pre-filled syringes and cartridges of an injectable medicament that are housed in an autoinjector assembly. In accordance with an embodiment of the claimed invention, an autoinjector device comprises:

a medication container;

a housing that internally receives the medication container, the housing further including a plurality of electrodes arranged circumferentially relative to the medication container; and a plurality of electrical contacts corresponding to the plurality of electrodes and in electrical communication therewith, the electrical contacts being accessible from the exterior of the autoinjector device, wherein a circuit between at least one pair of electrodes, measured at the electrical contacts, communicates data capable of determining a defect in the medication container. The medication container of the embodiment may be a cartridge or syringe or similar container typically used in autoinjectors pre-filled with liquid product. The plurality of electrodes comprise four equally-spaced electrodes in an alternative embodiment. In further embodiments, the plurality of electrodes may be positioned along an inner surface of the housing, embedded with the housing, or secured upon the medication container. The housing, in an alternative embodiment, may further comprise a removable cap portion, or otherwise by openable along an end whereby the needle attached to the medication container is accessible to dispense liquid product into a user. Further embodiments of the autoinjector device include an actuator assembly standard in the art for dispensing liquid from the medication container.

In accordance with another embodiment of the claimed invention an autoinjector assembly has a test circuit for detecting a defect of a pre-filled syringe, the autoinjector assembly comprising:

a housing having a substantially cylindrical shape;

a pre-filled syringe disposed within the housing, including a plunger movable within the syringe, a needle operably attached to the syringe, and a liquid product contained within the syringe to be dispensed through the needle;

an actuating assembly disposed within the housing operably connected to the plunger to dispense the liquid product from the syringe through the needle;

a plurality of electrodes disposed circumferentially around the syringe and extending along the length of the syringe; and a plurality of electrical contacts corresponding to the plurality of electrodes and in electrical communication therewith, the plurality of electrical contacts exposed through the exterior surface of the housing, wherein a voltage applied to the electrical contacts provides a measurement of syringe integrity.

In accordance with another embodiment of the claimed invention, a method of testing the integrity of an autoinjector device comprises a medication container, a housing that receives the medication container, the housing including a plurality of electrodes arranged circumferentially relative to the medication container, and a plurality of electrical contacts corresponding to the plurality of electrodes and in electrical communication therewith, the method comprising:

applying a voltage to at least one first contact and measuring the current at least one second contact; and determining the integrity of the medication container of the autoinjector device in accordance with the measured electrical current. The medication container of the embodiment may be a cartridge or syringe or similar container typically used in autoinjectors pre-filled with liquid product. The plurality of electrodes comprise four equally-spaced electrodes in an alternative embodiment. In further embodiments, the plurality of electrodes may be positioned along an inner surface of the housing, embedded with the housing, or secured upon the medication container. The housing, in an alternative embodiment, may further comprise a removable cap portion, or otherwise by openable along an end whereby the needle attached to the medication container is accessible to dispense liquid product into a user. Further embodiments of the autoinjector device include an actuator assembly standard in the art for dispensing liquid from the medication container.

In accordance with yet another embodiment of the claimed invention, a method of testing the integrity of a pre-filled syringe in an autoinjector, the autoinjector including a plurality of electrodes disposed circumferentially around the syringe and extending along the length of the syringe and a plurality of electrical contacts corresponding to the plurality of electrodes, comprises:

applying a voltage to a first contact of the plurality of electrical contacts and recording a measurement of the current at a second contact of the plurality of electrical contacts, the first contact and second contact being provided on opposite sides of the syringe;

applying a voltage to a third contact of the plurality of electrical contacts and recording a measurement of the current at a fourth contact of the plurality of electrical contacts, the third contact and fourth contact being provided on opposite sides of the syringe;

applying a voltage to the second contact and recording a measurement of the current at the first contact;

applying a voltage to the fourth contact and recording a measurement of the current at the third contact; and comparing the recorded measurements of the applied voltages to corresponding measurements of a non-defective pre-filled syringe to determine the integrity of the pre-filled syringe under test.

These and other aspects of, and advantages with, the present invention will become apparent from the following detailed description of the invention and from the accompanying drawings.

BRIEF DESCRIPTION OF THE SEVERAL VIEWS OF THE DRAWINGS

The present invention is better understood in light of the following drawings, wherein.

Figure 1:
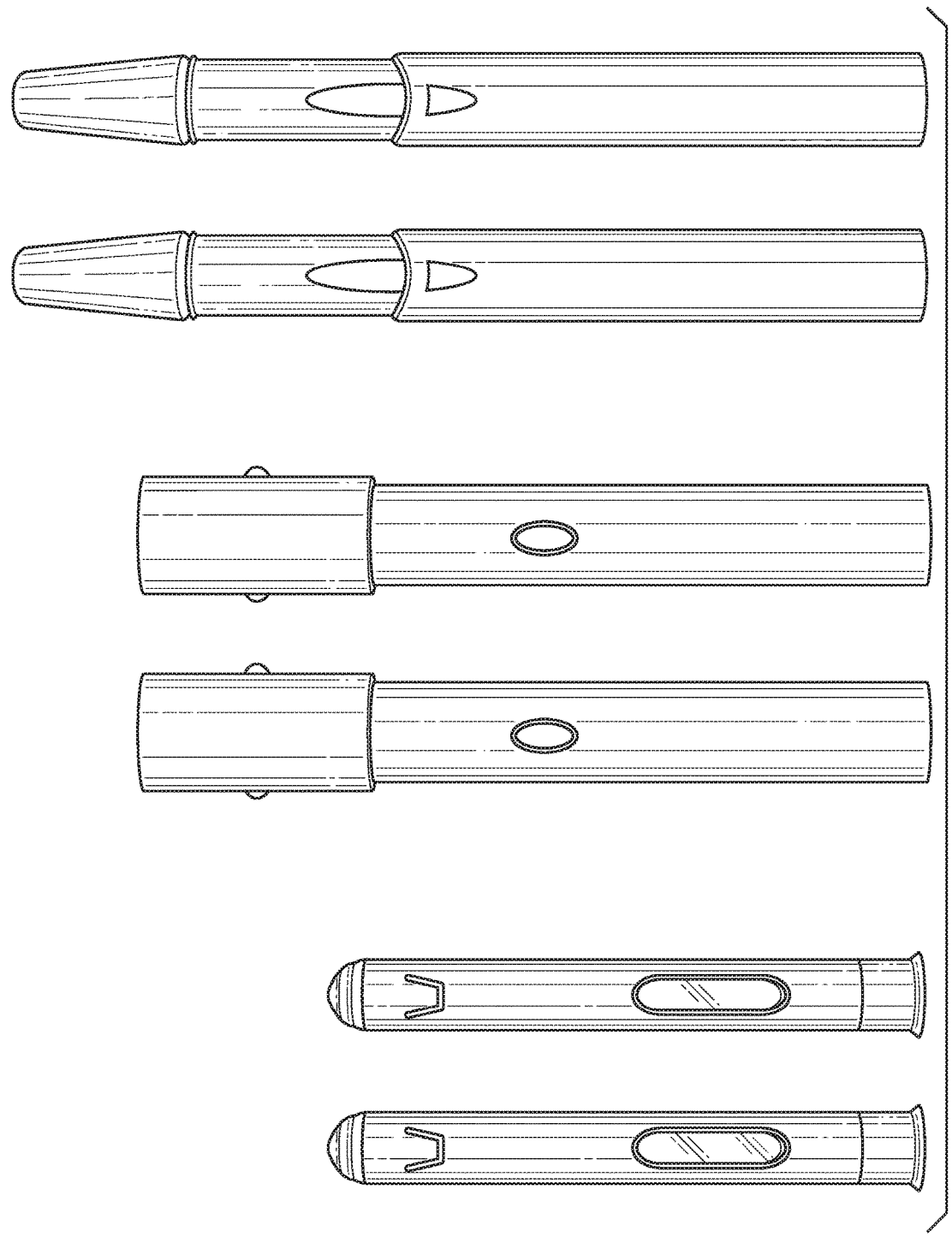
FIG. 1 is an illustration of a side view of several different prior art autoinjectors.

A better understanding of the present invention will be had from a detailed description of the embodiments of the invention.

DETAILED DESCRIPTION OF THE INVENTION

The present invention solves the problem of testing container integrity of medical containers housed inside of autoinjectors by providing an autoinjector assembly that acts as a HVLD test chamber, wherein the autoinjector includes a plurality of electrodes within a housing of the autoinjector and which are electrically connectable to remaining components of a HVLD leak detection apparatus, such as a high voltage rectifier, pulse autotransformer, DC voltage power supply, detection board, programmable logic controller, and display.

Embodiments will be described in detail with reference to the accompanying drawings. The inventive concepts, however, may be embodied in various different forms, and should not be construed as being limited only to the illustrated embodiments. Rather, these embodiments are provided as examples so that this disclosure will be thorough and complete, and will fully convey the inventive concepts to those skilled in the art. Accordingly, because known processes, elements, and techniques are known by those of skill in the art, they are not always described with respect to some of the embodiments. Unless otherwise noted, like reference numerals denote like elements throughout the attached drawings and written description, and thus descriptions will not be repeated. In the drawings, the sizes and relative sizes of elements and regions may be exaggerated or simplified for clarity.

Unless otherwise defined, all terms (including technical and scientific terms) used herein have the same meaning as commonly understood by one of ordinary skill in the art to which this inventive disclosure belongs. It will be further understood that terms, such as those defined in commonly used dictionaries, should be interpreted as having a meaning that is consistent with their meaning in the context of the relevant art and/or the present specification and will not be interpreted in an idealized or overly formal sense unless expressly so defined herein.

In the following description the term "medication container" refers to containers, cartridges, syringes, and the like, with or without a fixed needle assembly, that are pre-filled with an injectable liquid medication for use with an autoinjector device or similar drug delivery system. Illustrations of exemplary, known autoinjectors are provided in FIG. 1 to illustrate the variance in size and shape among autoinjectors. Technical disclosures of exemplary autoinjectors are provided in the Background of the Invention section of the present disclosure.

Figure 2A:
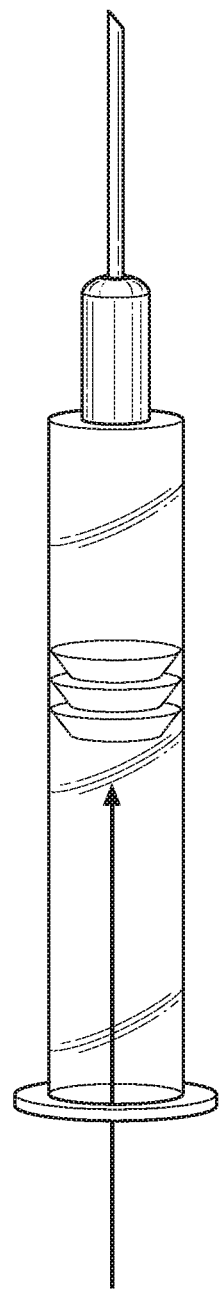
FIG. 2A is an illustration of a side view of a syringe, as commonly used in autoinjectors.
Figure 2B:
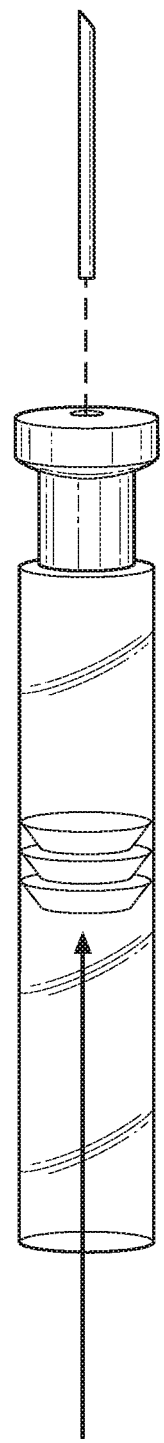
FIG. 2B is an illustration of a side view of a cartridge, as commonly used in autoinjectors.

The present invention does not limit or confine the improved autoinjector embodiments described herein to a particular size or shape. The present invention may be practiced in different lengths, diameters, and shapes, similar to the variances shown in FIG. 1. As most liquid medication containers are cylindrical in shape, embodiments of the autoinjector described herein are likewise generally cylindrical in shape to accommodate said medication containers. A syringe with a fixed needle assembly and plunger, exemplary of a type of medication container that may be found in an autoinjector device, is shown in FIG. 2A. A cartridge without a fixed needle assembly and with a plunger, exemplary of a type of medication container that may be found in an autoinjector device, is shown in FIG. 2B.

Figure 3A:
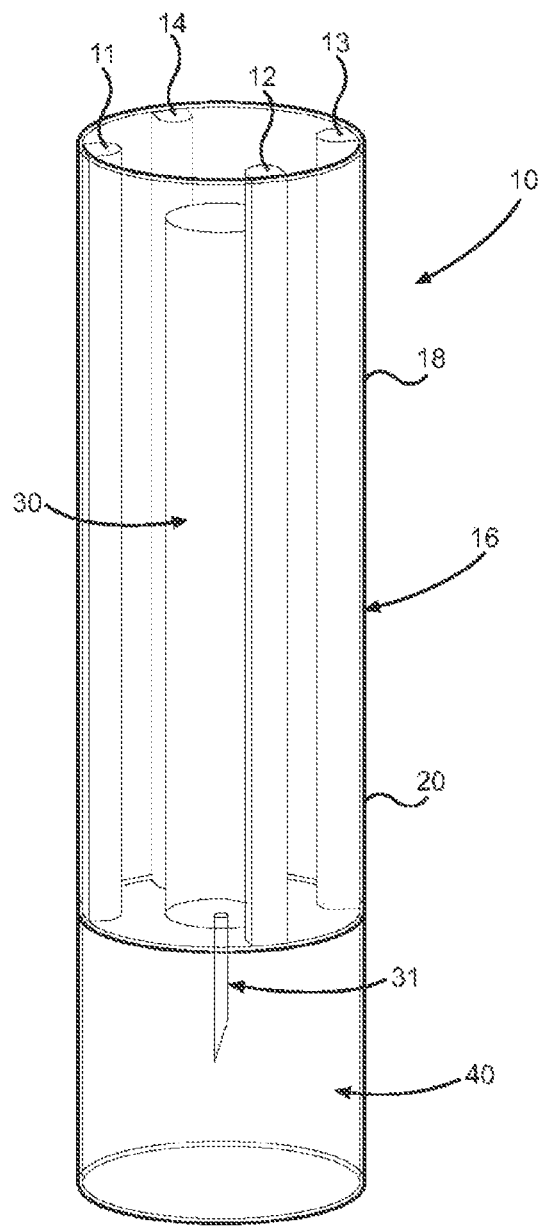
FIG. 3A is a side perspective view of simplified representation of an embodiment of an autoinjector according to the present invention.

An embodiment of an improved autoinjector 10 including electrodes for a HVLD testing circuit is provided in FIG. 3A. The autoinjector 10 includes a housing 16, which is generally hollow, and a medication container 30 disposed within the housing. As previously discussed, the housing 16 is substantially cylindrical to accommodate the generally cylindrical medication container 30. The housing 16 is typically made of a plastic material, but may be made of another appropriate material known in the medical device field to ensure product integrity. The medication container 30 has a needle 31 or similar structure, either fixed or unfixed, to transmit liquid medication, not shown, from the medication container to a user.

An actuator assembly with a plunger, or similar device, to force medication out from the medication container through the needle is also typically provided. The actuator assembly and plunger are not shown in FIG. 3A. The embodiments of an autoinjector described herein use known actuator assemblies for dispensing the liquid medication product from the medication container to users. These known elements and structures are not illustrated in the representation of FIG. 3A to reduce cluttering in the representation and to more clearly show the inventive aspects of embodiment.

A cap 40, or other similar removable or openable portion of the housing 16, protects the needle 31 of the medication container 30 during distribution and when the autoinjector 10 is not in use. The cap 40 can be removed or opened during use of the autoinjector 10, exposing the needle 31 for insertion or interaction with a user.

In the present invention, a plurality of electrodes 11, 12, 13, and 14 comprised of strips of conductive material are provided around the circumference of the housing 16, extending lengthwise along the housing and parallel to the length of the medication container 30, to facilitate HVLD testing of the medication container. In the embodiment illustrated in FIG. 3A, four electrodes are disposed around the circumference of the cylindrical medication container 30 at increments of approximately 90 degrees. The electrodes are preferably placed along an interior surface 18 of the housing 16, as shown in FIG. 3A, or embedded within the housing 16, but may also connected to an exterior surface of the medication container 30.

In operation of embodiments of a corresponding HVLD test method, described herein, pairs of diametrically-opposed electrodes provide a source electrode that receives a voltage, and a ground electrode. It will be recognized that a single pair of electrodes may be sufficient to provide measurement data, but may not be optimal to properly ensure accurate and precise determinations of medication container integrity. It will also be recognized that additional pairs of electrodes may be implemented for additional measurement data.

Figure 3B:
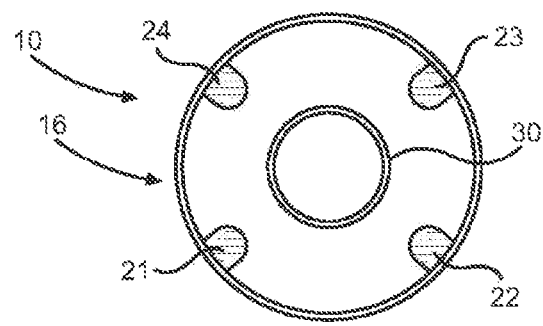
FIG. 3B is a top view of the embodiment of FIG. 3A.

As illustrated in FIG. 3B, four electrical contacts 21, 22, 23, and 24, corresponding to each electrode 11, 12, 13, and 14, respectively, are provided at an end of the housing 16 such that the contacts are accessible from the exterior of the autoinjector by an HVLD test instrument, whereby each of the electrodes 11, 12, 13, and 14 are in electrical communication with the HVLD test instrument via the respective electrical contact. It is appreciated that the number of electrical contacts will vary according to the number of electrodes present in a particular embodiment of the autoinjector. Further, it is appreciated that the location of the contact points along the housing 16 may vary, so long as each contact point is in electrical communication with a corresponding electrode.

In other embodiments of an autoinjector, the electrodes 11, 12, 13, and 14 could be arranged in a variety of opposing pair positions. While four or more electrodes is ideal to reduce proximity to a potential defect, in some embodiments the present invention may require only one electrode pair to detect a defect. Further embodiments of an autoinjector may include more than four electrodes. In yet further embodiments, each electrode of the plurality of electrodes is formed as a complete ring around the medication container, instead of linear, parallel electrodes illustrated in FIG. 3A. In such an embodiment, instead of opposing electrodes, the inspection probe and detection probe voltages would be applied to non-neighboring electrode rings to measure the resulting circuit thereby detecting a defect in the medication container. Each electrode of the electrode pair under test should not be in close proximity to one another, and must require the sample to either bridge the circuit in the event of a defect or not bridge the circuit. If the electrodes are too close they do not have the resisting barrier between them. This would cause an arc between the electrodes without passing any current through the sample.

HVLD testing of embodiments of the autoinjector involves applying a high voltage to pairs of electrodes by corresponding test probes via corresponding electrical contacts, with one test probe being an inspection probe and the other test probe being a detection probe. The medication container within the autoinjector 10 has a specific impedance and resistance. The resulting current through a non-defective medication container would be known prior to testing as a standard. Upon application of the voltage, if the container should have a leak, a discharge current will flow through a pinhole, crack, or defective seal into the medication container and will result in a loss of the specific impedance. A signal through the product is then detected by the detection probe. The resulting current through a defective container will result in a current with different value due to the loss of the specific impedance. Detecting the change in this current enables detecting the presence of a defect. A defective container will have a larger electric current present than a container without defect. The difference between the known standard and measured electric currents determines whether the container is defective.

Figure 4:
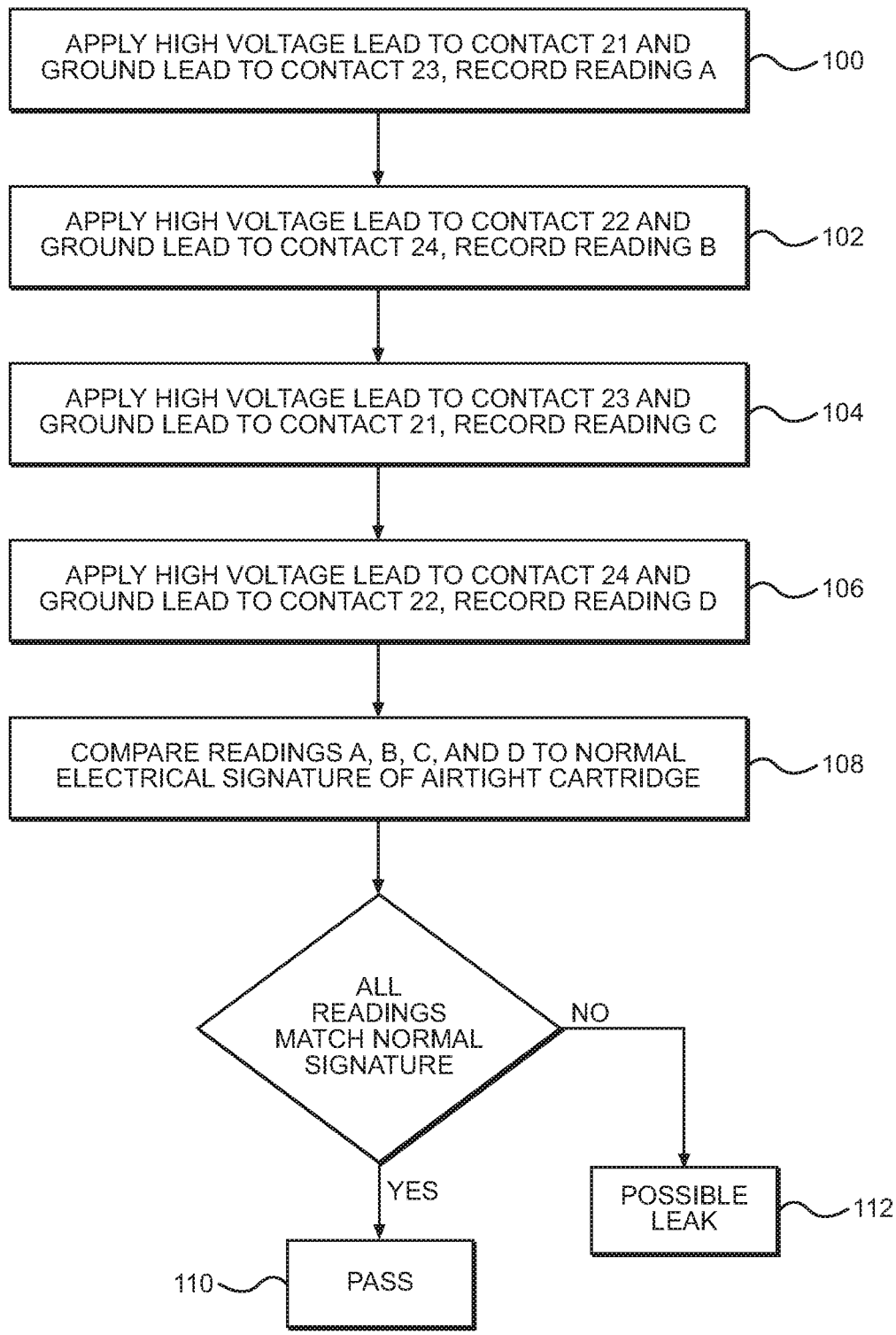
FIG. 4 is an illustration of a flow chart of an embodiment of a method for testing an autoinjector according to the present invention.

The impedance and/or resistance is measured for each combination of electrode pairs, thus in the embodiment shown in FIG. 3A, a high voltage is applied to each quadrant along the length of the cartridge. FIG. 4 illustrates a process for applying a voltage around the circumference of the medication container based upon the autoinjector embodiment of FIG. 3A at the contacts using an inspection probe (voltage) and a detection probe (ground). In step 100, reading A is a measurement produced through application of voltage to inspection electrode 11 via contact 21 and detected by detection probe 13 via contact 23. In step 102, reading B is a measurement produced through application of voltage to inspection electrode 12 via contact 22 and detected by detection probe 14 via contact 24. In step 104, reading C is a measurement produced through application of voltage to inspection electrode 13 via contact 23 and detected by detection probe 11 via contact 21. In step 106, reading D is a measurement produced through application of voltage to inspection electrode 24 via contact 14 and detected by detection probe 12 via contact 22. In step 108, each measurement A, B, C, and D is compared to the known electrical signatures of a non-defective container, for example, by a detection circuit. Integrity of the medication container can be then be determined. A medication container is not defective in step 110 if the measured readings A, B, C, and D are sufficiently similar compared to standard measurements for non-defective medical containers. A leak is detected in step 112 if the measured readings A, B, C, and D are different compared to standard measurements for non-defective medical containers. In further embodiments, this process may be altered in response to differing numbers of electrodes present.

Simplified methodologies for HVLD testing of a medication container are now described. However, the described methodologies should not be considered to limit or constrain the present invention to the following description. One of ordinary skill in the art recognizes that the detection of a leak in the medical container of the autoinjector cartridge through the measurement of electrical properties may be achieved by other devices and methods. Accordingly, any known or future methods of HVLD testing are contemplated as suitable alternatives to the exemplary methodologies shown and described herein, such they may be incorporated into the claimed invention without departing from the scope thereof.

Example 1

A generated high-voltage is applied to the medication container filled with liquid product through inspection probe. The high-voltage is generated by a high-voltage generation circuit and a pulse autotransformer or a pulse transformer and a high-voltage rectifier, for example, electrically connected to electrodes of the autoinjector via the respective electrical contacts. If the medication container should have a leak, a discharge current will flow through the pinhole, crack, or defective seal into the medication container. A signal through the liquid medication product is then detected by the detection probe. Detecting the change in this current enables the presence of a defect to be recognized.

Figure 5A:
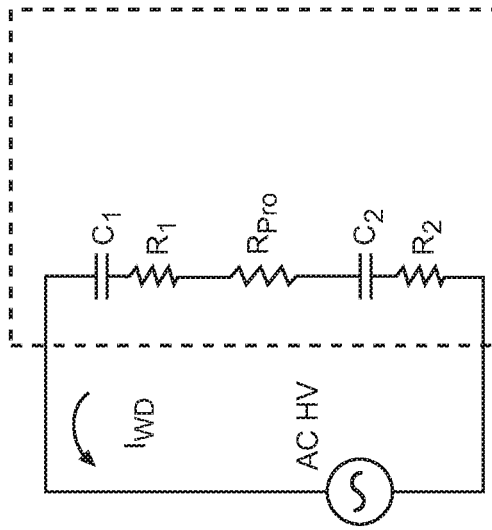
FIG. 5A is an illustration of a conventional HVLD test on a medication container without a leak.
Figure 5B:
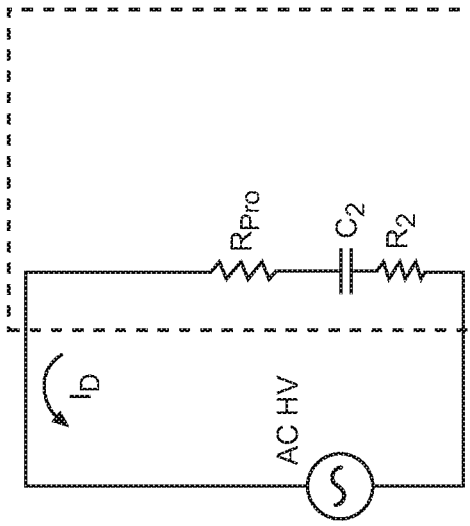
FIG. 5B is an illustration of a simplified electrical equivalent circuit of the convention HVLD test of FIG. 5A.
Figure 5C:
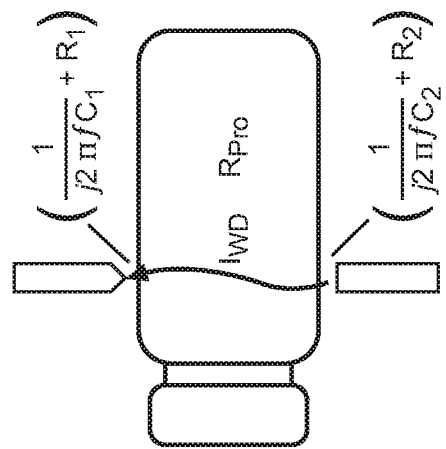
FIG. 5C is an illustration of a conventional HVLD test on a medication container with a leak.
Figure 5D:
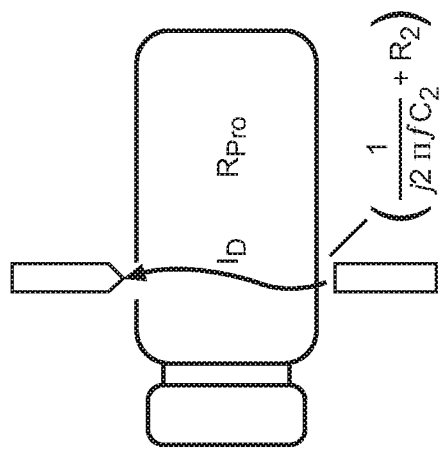
FIG. 5D is an illustration of a simplified electrical equivalent circuit of the convention HVLD test of FIG. 5C.

The principle of the HVLD by using AC high-voltage is illustrated in FIGS. 5A-5D. FIGS. 5A and 5B correspond to a HVLD test on a container without a leak. FIGS. 5C and 5D correspond to a HVLD test on a container with a leak. FIGS. 5A and 5C both illustrate the testing of a container with a single pair probes. FIGS. 5B and 5D show a simplified electrical equivalent circuit of the conventional HVLD system tests based on a pure AC high-voltage shown in FIGS. 5A and 5C, respectively. The following provides a legend for referring to FIGS. 5A through 5D:

$C_1$, $R_1$—Specific capacitance and resistor of #1 wall of medication container $C_2$, $R_2$—Specific capacitance and resistor of #2 wall of medication container $R_{Pro}$—Specific high-Ohm resistance of liquid product inside medication container f—Frequency of AC high-voltage $I_{WD}$—Current through a medication container without defect $I_D$—Current through a defective medication container It is important to note that $C_1$, $R_1$, $C_2$, $R_2$, and $R_{Pro}$ are variables and change depending on the amplitude of the applied AC high-voltage, material characteristics (such as dielectric strength of the medication container and liquid product contained therein), and the conductivity of the liquid product. Basically the higher the applied voltage is, the lower the impedances of $C_1$, $R_1$, $C_2$, $R_2$, $R_{Pro}$. The risk of applying too large of a voltage is the ionization of the air, causing the high-voltage to arc or spark over the impedances listed above and creating what appears as a false leak. So in any HVLD technology it is necessary to reach the highest possible voltage (to get better sensitivity of the leak detection) without sparking around the medication container to break down the insulation of the medication container and the liquid product inside the medication container.

The current through a medication container without defect can be found as follows:

$$I_{WD} = \frac{ACHV}{R_{Pro} + Z_1 + Z_2} \tag{1}$$

Wherein $$Z_1 = \frac{1}{j2\pi f C_1} + R_1 \tag{2}$$

and $$Z_2 = \frac{1}{j2\pi f C_2} + R_2 \tag{3}$$

When a leak is present one of the capacitors will be missing. The current through the defective medication container can be found as follows:

$$I_D = \frac{ACHV}{R_{Pro} + Z_1} \tag{4}$$

A defective medication container will have a larger electric current present ($I_D$) than a medication container without defect ($I_{WD}$). The difference between the electric currents determines whether the medication container is defective.

$$\Delta I = I_D I_{WD} \tag{5}$$

Example 2

Other systems and methods for HVLD are disclosed in the Applicant's international application no. PCT/US2016/056976, published as WO 2017136007 A1. In these embodiments, the existence of a leak in a medication container is determined by generating an AC high voltage with a DC high voltage offset in a circuit. The inspection probe applies the AC high voltage with the DC high voltage offset to the medication container. Current flow through the medication container is then detected by the detection probe. A detection board then processes the current flow and sends the processed signal to a programmable logic controller which determines if a leak is present in the medication container.

Whereas the method and device of the referenced application employ a separate testing apparatus to test lone medication containers, voltage is applied to electrodes incorporated in embodiment of autoinjectors described herein via corresponding electrical contacts. When AC voltage with the DC high-voltage offset is used for leak detection, the product inside the medication container without defect is not exposed to the applied DC high-voltage directly and exposed only to a much lower voltage. This is because the medication containers are typically made of insulators such as glass and plastic which are capacitive in nature. Therefore the glass and plastic containers can be modelled as capacitors in parallel with very high-Ohm resistors. The capacitors block the applied DC high-voltage fully and the high-Ohm resistors attenuate the applied DC high-voltage strongly.

Figure 6A:
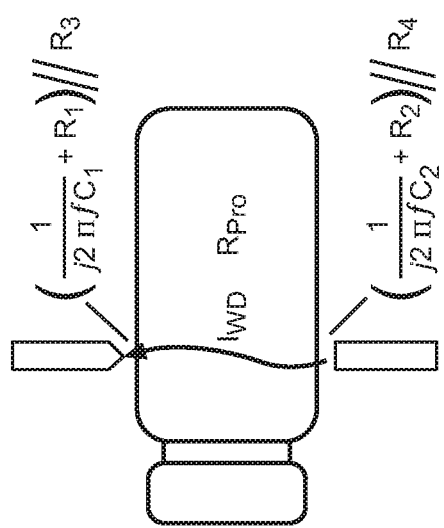
FIG. 6A is an illustration of a HVLD using AC high voltage with a DC high voltage offset on a medication container without a leak.
Figure 6B:
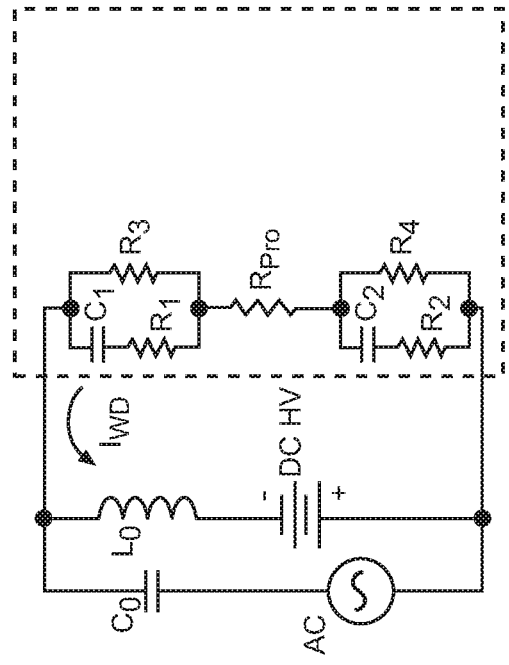
FIG. 6B is an illustration of a simplified electrical equivalent circuit of the HVLD using AC high voltage with a DC high voltage test of FIG. 6A.
Figure 6C:
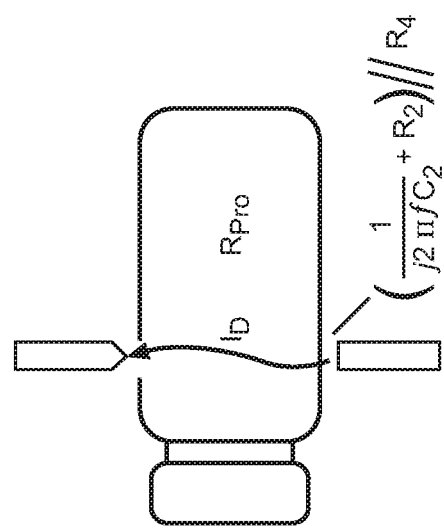
FIG. 6C is an illustration of a HVLD using AC high voltage with a DC high voltage offset on a medication container with a leak.
Figure 6D:
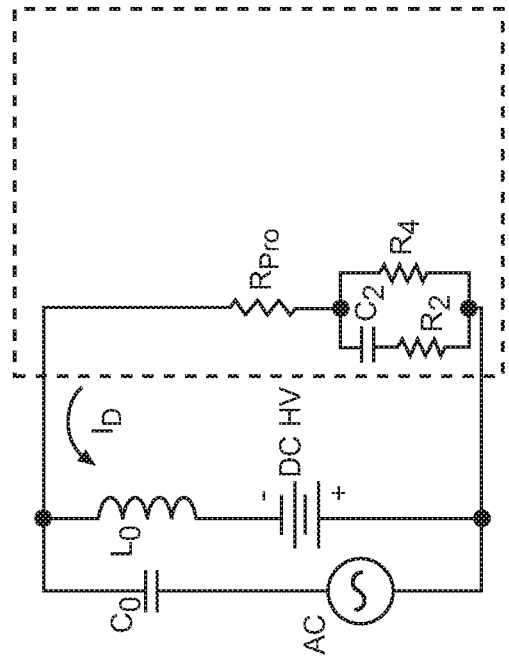
FIG. 6D is an illustration of a simplified electrical equivalent circuit of the HVLD using AC high voltage with a DC high voltage test of FIG. 6C.

HVLD technology based on ADHV (alternating direct high voltage) is illustrated in FIGS. 6A-6D. FIGS. 6A and 6B correspond to a HVLD-ADHV test on a container without a leak. FIGS. 6C and 6D correspond to a HVLD-ADHV test on a container with a leak. FIGS. 6A and 6C both illustrate the testing of a container with a single pair probes. FIGS. 6B and 6D show a simplified electrical equivalent circuit of the HVLD-ADHV system test of FIGS. 6A and 6C, respectively. The following provides a legend for referring to FIGS. 6A through 6D:

$C_1$, $R_1$—Specific capacitance and resistor of #1 wall of container $C_2$, $R_2$—Specific capacitance and resistor of #2 wall of container $R_3$—Specific high-Ohm resistance of #1 wall of container $R_4$—Specific high-Ohm resistance of #2 wall of container $R_{Pro}$—Specific high-Ohm resistance of liquid product inside container f—Frequency of AC voltage $L_0$—Ideal inductor in the simplified equivalent circuit for blocking AC current $C_0$—Ideal capacitor in the simplified equivalent circuit for blocking DC current $I_{WD}$—Current through a container without defect $I_D$—Current through a defective container The products inside the containers are only exposed to the DC high-voltage directly in presence of a defect or defects in the containers inspected. Since the HVLD technology based on an ADHV applies both AC and DC voltages, both AC and DC currents flow through the container inspected. The total current can be found as sum of AC and DC currents. In the simplified electrical circuit, the AC current can flow through all components in the circuit while the DC current can only flow through the path without capacitors.

It is important to note that the $C_1$, $R_1$, $C_2$, $R_2$, $R_3$, $R_4$, $R_{Pro}$ are variables and change depending on the amplitude of the applied AC voltage, level of the applied DC high-voltage offset, material characteristics such as dielectric strength of the container and liquid product, and the conductivity of the liquid product. $I_{WD}$, the total current through a container without defect can be found as in equation (6) where the $1^{st}$ term in the equation is for AC current and $2^{nd}$ is for DC. The inductor $L_0$ and capacitor $C_0$ are omitted here because they are the equivalent circuit of the test system's signal excitation circuitry and not part of the equivalent model of the product.

$$I_{WD} = \frac{AC}{R_{Pro} + Z_1 + Z_2} + \frac{DCHV}{R_{Pro} + R_3 + R_4} \quad (6)$$

Wherein $$Z_1 = \frac{\left(\frac{1}{j2\pi fC_1} + R_1\right) * R_3}{\left(\frac{1}{j2\pi fC_1} + R_1\right) + R_3} \quad (7)$$

and $$Z_2 = \frac{\left(\frac{1}{j2\pi fC_2} + R_2\right) * R_4}{\left(\frac{1}{j2\pi fC_2} + R_2\right) + R_4} \quad (8)$$

If a leak is present the $R_1$, $R_3$ and $C_1$ are missing and therefore equal to zero. Then $I_D$, the current through a defective container can be found as follows:

$$I_D = \frac{AC}{R_{Pro} + Z_2} + \frac{DCHV}{R_{Pro} + R_4} \quad (9)$$

It can be seen from equations (1) and (4) that the electric current $I_D$ through a defective container is greater than the current $I_{WD}$ through a container without defect. This enables detection of a leak or pinhole in containers according to the equation (10).

$$\Delta = I_D - I_{WD} \quad (10)$$

The invention having been disclosed in connection with the foregoing embodiment and examples, additional variations will now be apparent to persons skilled in the art. Various modifications and variations to the above described autoinjector integrity testing systems and methods can be made without departing from the scope of the present invention. The invention is not intended to be limited to the embodiments specifically mentioned and accordingly reference should be made to the appended claims rather than the foregoing discussion of preferred embodiments and examples to assess the spirit and scope of the invention in which exclusive rights are claimed.

We claim:
1. An autoinjector device, comprising:
   a housing configured to internally receive a liquid product container, wherein the housing comprises:
      electrodes arranged around the liquid product container when the liquid product container is received by the housing, wherein the electrodes are substantially linear and positioned substantially parallel with a length of the liquid product container; and
      electrical contacts accessible from the exterior of the autoinjector device, wherein the electrical contacts are configured to be in electrical communication with the electrodes when the liquid product container is received by the housing and receive an applied voltage for detecting a leak in the liquid product container.
2. The autoinjector device of claim 1, further comprising an actuator device configured to dispense a liquid product contained within the liquid product container.
3. The autoinjector device of claim 1, wherein the electrodes comprise strips that extend lengthwise along the housing and parallel to the entire length of the liquid product container.
4. An autoinjector assembly, comprising:
   a housing;
   a liquid product container pre-filled with a liquid product and disposed within the housing;

electrodes disposed within the housing and around the liquid product container and extending along a length of the liquid product container;

electrical contacts accessible from the exterior of the autoinjector assembly, wherein the electrical contacts are configured to be in electrical communication with the electrodes; and a test circuit formed between one pair of the electrodes upon application of a voltage to at least one of the electrical contacts for detecting a leak in the pre-filled liquid product container.

5. The autoinjector assembly of claim 4, wherein the housing further comprises a removable portion to allow the liquid product to be dispensed to a user.

6. The autoinjector assembly of claim 4, wherein the electrodes comprise four electrodes, and the electrical contacts comprise four electrical contacts corresponding to the four electrodes.

7. The autoinjector assembly of claim 4, wherein the electrodes comprise strips extending along an entire length of the housing.

8. The autoinjector assembly of claim 4, wherein the electrodes are substantially circular and disposed circumferentially along an interior surface of the housing and around the liquid product container.

9. The autoinjector assembly of claim 4, wherein the electrodes are embedded within the housing.

10. The autoinjector assembly of claim 4, wherein the electrodes are disposed along an exterior surface of the liquid product container.

11. A method of detecting a leak in a pre-filled container in an autoinjector, the autoinjector comprising electrodes disposed around the container contained therein, the electrodes extending along a length of the container and electrical contacts configured to be in electrical communication with the electrodes, the method comprising:

applying a voltage to a first contact of the electrical contacts and recording a measurement of the current at a second contact of the electrical contacts, the first contact and second contact being provided on opposite sides of the container;

applying a voltage to a third contact of the electrical contacts and recording a measurement of the current at a fourth contact of the electrical contacts, the third contact and fourth contact being provided on opposite sides of the container;

applying a voltage to the second contact and recording a measurement of the current at the first contact;

applying a voltage to the fourth contact and recording a measurement of the current at the third contact; and comparing the recorded measurements of the applied voltages to corresponding measurements of a non-defective pre-filled container to detect a leak in the pre-filled container.

12. The method of claim 11, wherein the autoinjector further comprises a housing and the electrodes are disposed along the housing and the pre-filled container is disposed within the housing.

13. The method of claim 12, wherein the housing further comprises a removable portion to allow dispensing of a liquid held within the pre-filled container.

14. The method of claim 12, wherein the electrodes are disposed along an interior surface of the housing.

15. The method of claim 12, wherein the electrodes are embedded within the housing.

16. The method of claim 12, wherein the electrodes are disposed along an exterior surface of the pre-filled container.

17. The method of claim 11, wherein the electrodes comprise four electrodes, and the electrical contacts comprise four electrical contacts corresponding to the four electrodes.

18. A method of leak testing an autoinjector device comprising a medication liquid product container, a housing that receives the medication liquid product container, the housing comprising electrodes arranged around the medication liquid product container, wherein the electrodes are substantially linear and positioned substantially parallel with a length of the liquid product container, and electrical contacts configured to be in electrical communication with the electrodes, the method comprising:

applying a voltage to a first contact of the electrical contacts and measuring the current at a second contact of the electrical contacts; and detecting a leak in the medication liquid product container of the autoinjector device based on the measured electrical current.

19. The method of claim 18, wherein the medication liquid product container is a syringe or a cartridge, and the medication liquid product container is pre-filled and packaged with a liquid product.

* * * * *